United States Patent
Wu et al.

(10) Patent No.: US 10,682,299 B2
(45) Date of Patent: Jun. 16, 2020

(54) NANO COMPOSITE MATERIALS AND USE THEREOF

(71) Applicants: Chih-Tseng Wu, Taichung (TW); Chiu-Yung Hong, Taipei (TW); Chien-Ho Chen, Kaohsiung (TW)

(72) Inventors: Chih-Tseng Wu, Taichung (TW); Chiu-Yung Hong, Taipei (TW); Chien-Ho Chen, Kaohsiung (TW)

( * ) Notice: Subject to any disclaimer, the term of this patent is extended or adjusted under 35 U.S.C. 154(b) by 0 days.

(21) Appl. No.: 16/181,497

(22) Filed: Nov. 6, 2018

(65) Prior Publication Data
US 2019/0133900 A1    May 9, 2019

(30) Foreign Application Priority Data
Nov. 6, 2017 (TW) .............................. 106138330 A

(51) Int. Cl.
| | | |
|---|---|---|
| *A61K 8/19* | (2006.01) | |
| *A61K 8/64* | (2006.01) | |
| *A61Q 19/00* | (2006.01) | |
| *A61Q 7/00* | (2006.01) | |
| *A61K 8/02* | (2006.01) | |
| *A61Q 1/10* | (2006.01) | |

(52) U.S. Cl.
CPC .............. *A61K 8/19* (2013.01); *A61K 8/0241* (2013.01); *A61K 8/64* (2013.01); *A61Q 7/00* (2013.01); *A61Q 19/00* (2013.01); *A61K 2800/413* (2013.01); *A61Q 1/10* (2013.01)

(58) Field of Classification Search
CPC .............. A61Q 7/00; A61Q 1/10; A61K 8/64
See application file for complete search history.

(56) References Cited

FOREIGN PATENT DOCUMENTS

| | | | |
|---|---|---|---|
| CN | 102871864 A | 1/2013 | |
| CN | 106176500 A | 12/2016 | |
| TW | I433680 B | 4/2014 | |
| TW | I559939 B | 12/2016 | |
| WO | WO-2012143845 A2 * | 10/2012 | ............. A61K 38/06 |

OTHER PUBLICATIONS

Ramesh, A. et al. ("Peptides conjugated to silver nanoparticles in biomedicine—a 'value-added' phenomenon", Biomater. Sci. 2016, 4, 1713 (Year: 2016).*

* cited by examiner

*Primary Examiner* — Gina C Justice
(74) *Attorney, Agent, or Firm* — Harness, Dickey & Pierce, P.L.C.

(57) ABSTRACT

A nano composite material comprising: a biotinoyl tripeptide-1 nanosilver composite material which is conjugated by biotinoyl tripeptide-1 and nanosilver. The nano composite material of this technology can prevent hair loss, promote hair and eyelash growth, repair skin, etc.

8 Claims, 24 Drawing Sheets

NANO COMPOSITE MATERIALS AND USE THEREOF

CROSS-REFERENCE TO RELATED APPLICATIONS

This application claims priority to Taiwanese Patent Application No. 106138330, filed on Nov. 6, 2017. The entire contents of the application are hereby incorporated by reference.

FIELD

This following relates to a nano composite material and the use thereof, comprising: a biotinoyl tripeptide-1 nanosilver composite material. The nano composite material of this technology can prevent hair loss, promote hair and eyelash growth, repair skin, etc.

BACKGROUND

Conventional nano materials are extremely small in size and can be easily placed inside living bodies. In recent years, combining nano gold with biosystem is a popular research topic in the related areas of nano materials. Currently, there are composite materials made from nano particles and biomolecules such as, protein, DNA and biopolysaccharide. By making use of the characteristics of inter-biomolecules, they can be applied in gene therapy, biomarker, drug targeting or biological transportation.

Based on the definition of nanotechnology, the particle size of a nanosilver particle is between 1-100 nm. Prior art has disclosed that nanosilver is antibacterial and can repair skin wounds. Patent literature 1 "A composite of spherical silver nanoparticles and layered inorganic clay" disclosed using nanosilver for antibacterial effect.

However, there have been very few applications using this technique in preventing hair loss, promoting hair growth, eyelash growth, and in cosmetics and skin care products.

Moreover, biotinoyl tripeptide-1 is regarded as a kind of protein derivative. It provides a protective shield for the hair, and it penetrates the hair stem to enhance the hair and prevent hair loss at the same time. Vitamin B is an essential factor in human cell growth and many enzyme systems.

However, biotinoyl tripeptide-1 is difficult to be absorbed by human body under normal conditions.

Commercial anti-hair loss products only use biotinoyl tripeptide-1 and nanosilver respectively as one of their ingredients. They did not combine biotinoyl tripeptide-1 and nanosilver, wherein the composite material is easier to be absorbed by human and prevents hair loss more effectively.

In order to solve the problems of prior art, this technology uses the characteristics of biotinoyl tripeptide-1 and conjugate with nanosilver, which increases the exploitability of the nano particle composite. This technology provides a composite material of nanosilver and biotinoyl tripeptide-1, and creates a formula to prevent hair loss, promote hair and eyelash growth and skin repair that can be used in anti-hair loss, hair growth, eyelash growth products, cosmetics, and skin care products.

SUMMARY

An aspect relates to a nano composite material which is conjugated by biotinoyl tripeptide-1 and nanosilver. It can prevent hair loss, promote hair and eyelash growth, nourish skin, etc. In order to accomplish this purpose, this invention provides the following technical teachings.

A nano composite material, comprising: a biotinoyl tripeptide-1 nanosilver composite material which is conjugated by biotinoyl tripeptide-1 and nanosilver.

The nano composite material as described in the previous paragraph, wherein the biotinoyl tripeptide-1 nanosilver composite is analyzed in the form of nanosilver aqueous solution by an ultraviolet/visible spectrophotometer; the absorption spectrum has a specific absorption spectrum peak within 385 nm to 415 nm.

The nano composite material as described in any of the previous paragraphs, wherein the particle size of the biotinoyl tripeptide-1 nanosilver composite is between 20 nm to 100 nm.

The nano composite material as described in any of the previous paragraphs, wherein the Zeta potential of the biotinoyl tripeptide-1 nanosilver is greater than ±15 mv.

A topical preparation for skin, comprising the nano composite material as described in any of the previous paragraphs.

A compound to prevent hair loss, comprising the nano composite material as described in any of the previous paragraphs.

A solution for promoting hair growth, comprising the nano composite material as described in any of the previous paragraphs.

A solution for promoting eyelash growth, comprising the nano composite material as described in any of the previous paragraphs.

BRIEF DESCRIPTION OF THE DRAWINGS

Some of the embodiments will be described in detail, with references to the following Figures, wherein like designations denote like members, wherein.

DETAILED DESCRIPTION

The present invention will be further exemplified by the following examples, which are not to be seen as limiting. The embodiments and description are used for illustrating the details and effect of the present invention.

[Method of Preparing Biotinoyl Tripeptide-1 Nanosilver]

The steps of preparing biotinoyl tripeptide-1 nanosilver comprises:

Step A1: Mix the protectant, biotinoyl tripeptide-1 with silver nitrate for 10 to 40 minutes away from light to create the first mixed solution.

Step A2: Add reductant to the first mixed solution and stir for the first predetermined time to form the second mixed solution, wherein the first predetermined time can be 10 to 30 minutes.

Step A3: Add reductant to the second mixed solution and stir for second predetermined time to create biotinoyl tripeptide-1 nanosilver particles, wherein the second predetermined time can be 1 to 2 hours.

[Particle Size Distribution]

Figure 1:
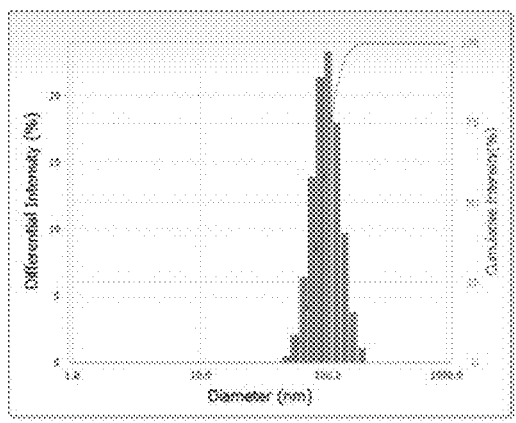
FIG. 1 is a distribution graph of the particle size of the biotinoyl tripeptide-1 nanosilver particle from the present invention.
Figure 1:
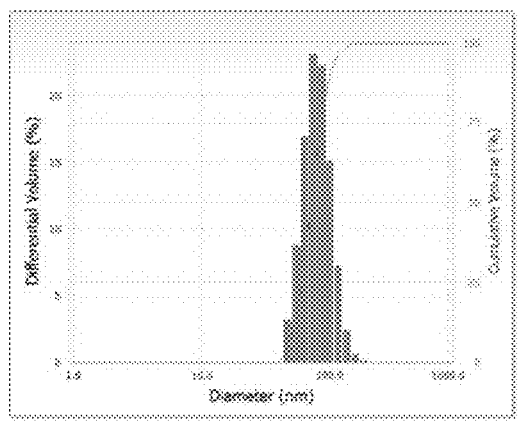
Figure 1:
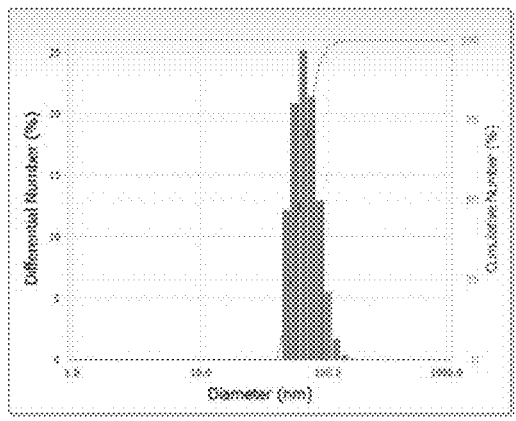
Figure 1:
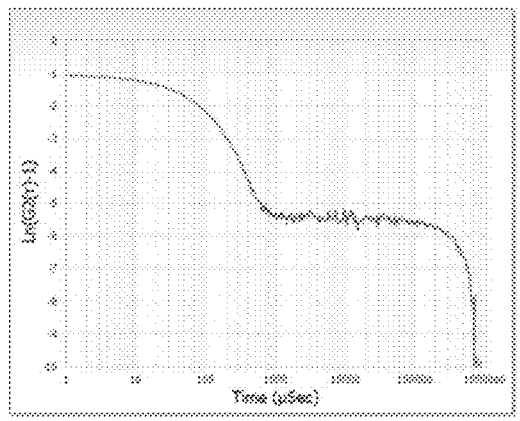

According to the definition of nano, particle size of a nanosilver particle is between 1 nm to 100 nm. Referring to FIG. 1, the particle size of biotinoyl tripeptide-1 nanosilver is at nano size, wherein the particle size may be within 20 nm to 100 nm, preferably within 30 nm to 95 nm, or more preferably within 40 nm to 90 nm, or even more preferably within 45 nm to 80 nm.

[Observation of Transmission Electron Microscope (TEM) View]

Figure 2:
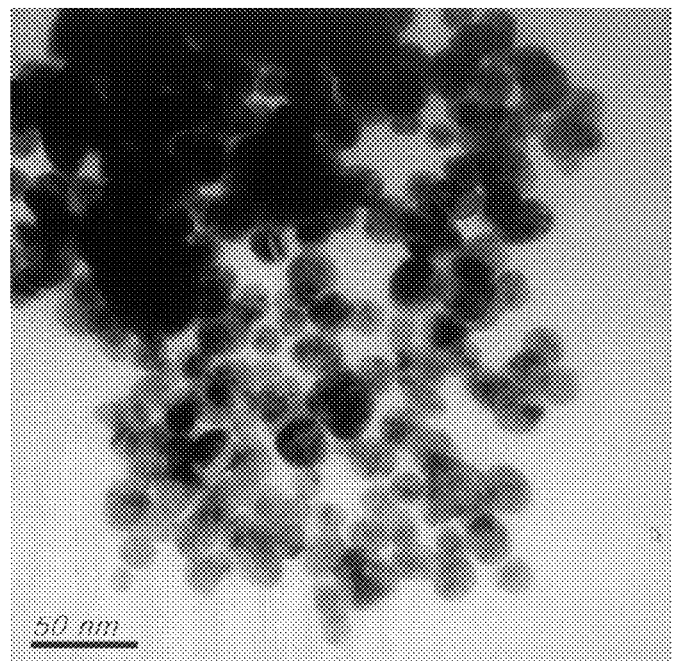
FIG. 2 is an image of the biotinoyl tripeptide-1 nanosilver from the present invention using a transmission electron microscope (TEM)

Referring to FIG. 2, the image of biotinoyl tripeptide-1 nanosilver is from observation by a transmission electron microscope.

This figure further confirms the particle size of biotinoyl tripeptide-1 nanosilver is less than 100 nm.

[Determination of Wavelength and Absorption Spectrum]

Figure 3:
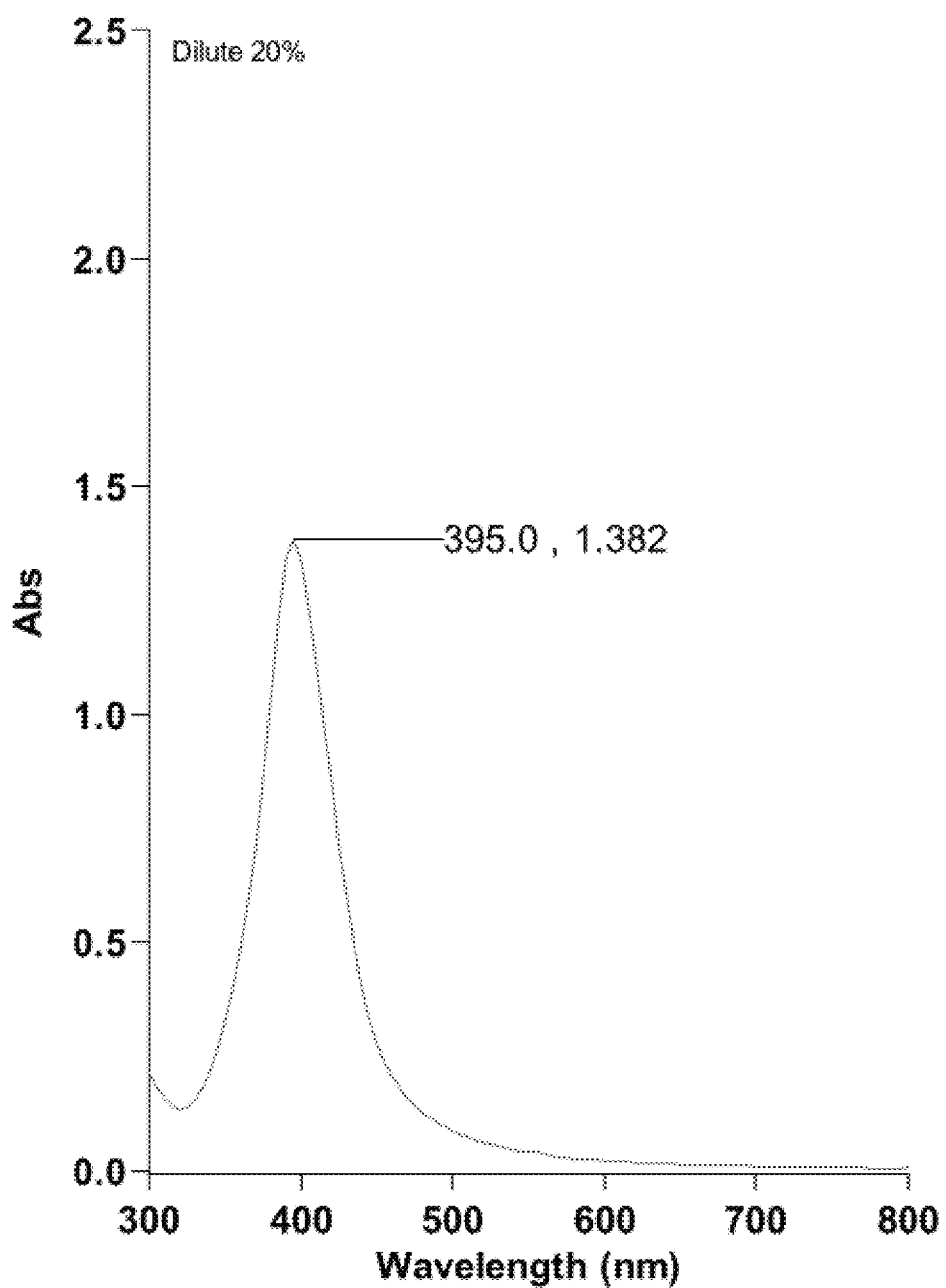
FIG. 3 is a curve diagram of the wavelength and absorption spectrum of the biotinoyl tripeptide-1 nanosilver from the present invention.

Referring to FIG. 3, the curve diagram of the wavelength and absorption spectrum of the biotinoyl tripeptide-1 nanosilver is shown.

This invention uses a spectrophotometer to determine the wavelength and absorption spectrum of the biotinoyl tripeptide-1 nanosilver in this invention, and determine if the wavelength of the nanosilver of the biotinoyl tripeptide-1 nanosilver is within the normal range of 395 nm to 415 nm.

As shown in FIG. 3, the wavelength of nanosilver of the biotinoyl tripeptide-1 nanosilver is preferably within 375 nm to 420 nm, or more preferably within 385 nm to 415 nm and the peak of the wavelength in the present invention is 395.0 nm. Therefore, the biotinoyl tripeptide-1 nanosilver particle is more stable and does not deteriorate easily.

[Diagram of Zeta Potential]

Figure 4:
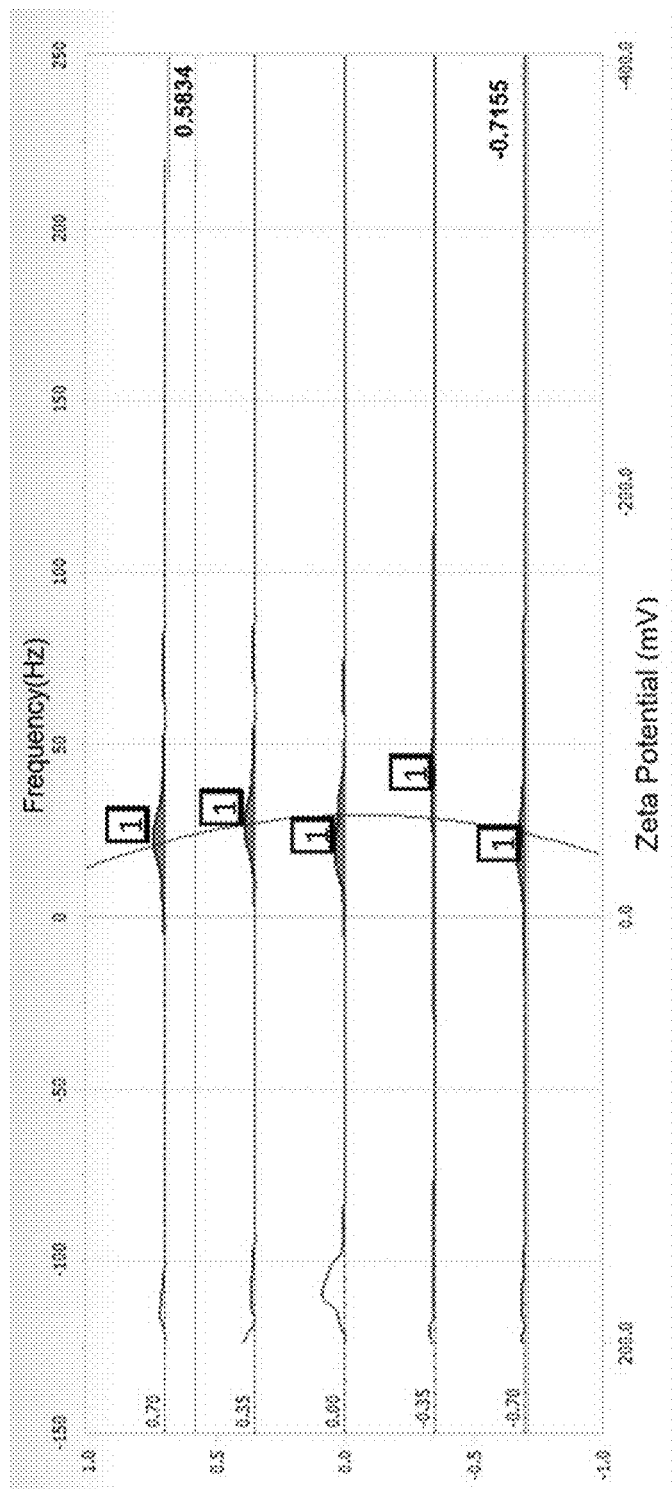
FIG. 4 is a diagram of Zeta potential of the biotinoyl tripeptide-1 nanosilver from the present invention.

FIG. 4 is the diagram of Zeta potential of the biotinoyl tripeptide-1 nanosilver, wherein Zeta potential is preferably greater than ±15 mv, or more preferably greater than ±20 mv, or greater than ±30 mv is the most ideal.

[Promotion of the Human Hair Follicle Dermal Papilla Cell Growth]

The influence of the biotinoyl tripeptide-1 nanosilver in present technology on human hair follicle dermal papilla cell growth is assessed.

Firstly, activate and cultivate human hair follicle dermal papilla cells (HFDPC), place the cells in an incubator saturated with water vapor at temperature 37±1° C., whereas the carbon dioxide concentration at 5±1%.

Then place different concentration of biotinoyl tripeptide-1 in cells and use MTT assay to evaluate the effect of cell growth. Repeat the experiment three times.

Analysis using statistical software is performed to estimate the significance of cell growth. (n=3, *p<0.05).

Figure 5:
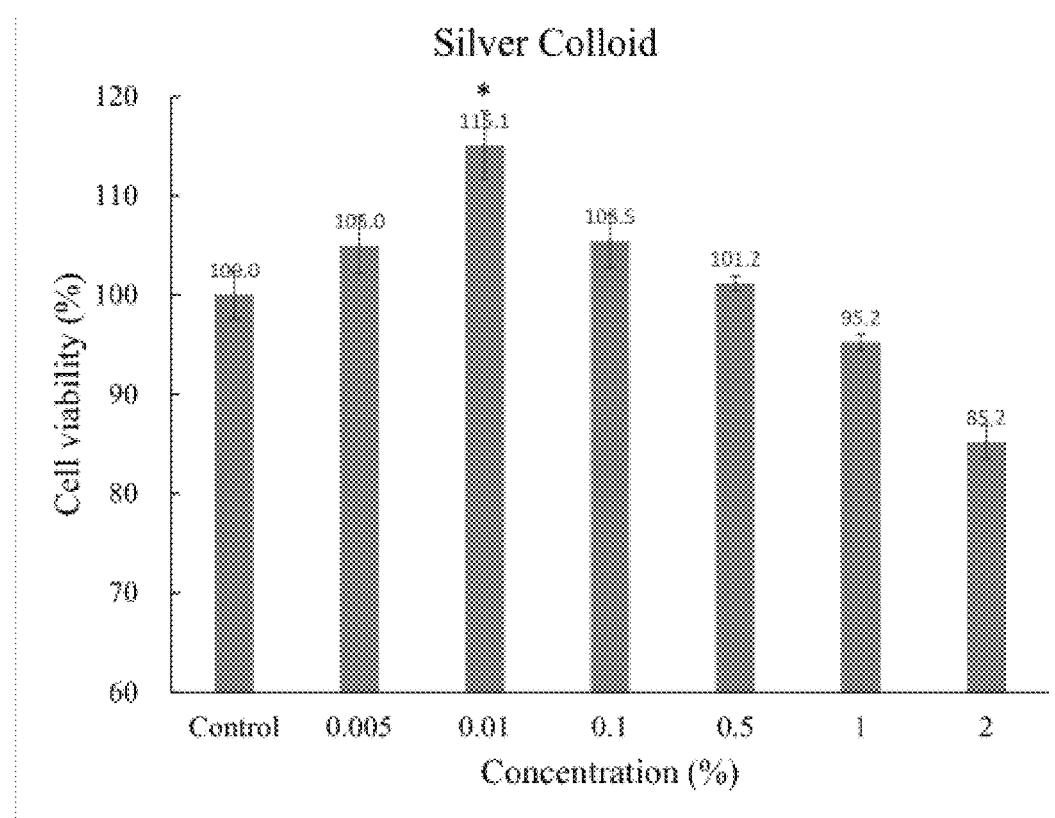
FIG. 5 is a concentration diagram of the human hair follicle dermal papilla cell growth promoted by the biotinoyl tripeptide-1 nanosilver from the present invention.

The results are shown in FIG. 5. The concentration of the biotinoyl tripeptide-1 nanosilver at 0.005% can promote human hair follicle dermal papilla cells (HFDPC) growth to 105%; concentration of the biotinoyl tripeptide-1 nanosilver at 0.01% is more effective and can promote human hair follicle dermal papilla cells (HFDPC) growth to 115.1%.

The following relates to the evaluation of human hair growth and hair care after using the hair care product which contains the biotinoyl tripeptide-1 nanosilver of the present invention, comprising: hair quantity, hair thickness and sebum level on scalp.

[Sample Preparation]

Mix the biotinoyl tripeptide-1 nanosilver of the present invention with other conventional hair care solution to create the hair care product of this invention (hereinafter referred to as the "hair care product").

Participant selection criteria:

Inclusion criteria:

Age 20 to 60, male and female with hair loss or rough hair or frizzy hair issues.

No usage of medication a week prior to testing, meaning no Finasteride intake (such as Propecia or Proscar) and no hair growth medication Minoxidil (such as Regaine) on target skin (scalp) is allowed.

Individuals who understand the process and measuring methods.

Exclusion criteria:
Pregnant women.
Patients with skin diseases.
Patients with heart disease, diabetes, cancer or other major diseases.
Allergic to hair care products.
Easily allergic to alcohol.
Steps and Equipment
Measuring equipment:
Scalp hair analysis device (ARAM HUVIS; model: ASG)
Sebum level detector (Sebumeter®; model: SM815)
Measuring areas:
Scalp hair analysis device: top of the head, center of the front hairline
Sebum level detector: top of the head.
[Measuring Procedure]
Firstly, users apply the hair care product every alternative day after washing hair. The hair care product of this invention is sprayed evenly on top of scalp (8 times in total, approximately 2 ml) and massage scalp for 3 minutes to absorb. There is no need to wash afterwards and the treatment is 12 weeks in total.

Moreover, shampoos or conditioners that promote hair growth, prevent hair loss, control oil secretion are forbidden during the trial period.

Before the measuring procedure, participants will stay in a room with constant humidity of 50±10% and constant temperature at 20±2° C. for 30 minutes. Then the scalp hair analysis device and sebum level detector are used to measure the condition of the participants. Meanwhile, a scalp hair analysis device is used to film and record the condition of hair and scalp of participants.
[Data Analysis]

20 participants aged 20 to 60 were recruited based on the inclusion and exclusion criteria of participants, including 6 males and 14 females.

After confirming there is no allergy reaction among the participants, the treatment begins and it is non-invasive. Measurement was performed before and after the treatment. After the treatment, ANOVA test and paired student's T test were performed to analyze the experiment result. When p-value<0.05, it indicates there is significant difference before and after the treatment, and pictures were taken before and after the treatment to illustrate the difference (referring to FIGS. 6 to 11).
[Hair Quantity Test (Top of the Head)]

This test uses the 60× lens of the scalp hair analysis device to shoot the top of participant's head. The device can automatically select an area for calculation and calculate the hair quantity per square centimeter in the selected area.

Figure 6:
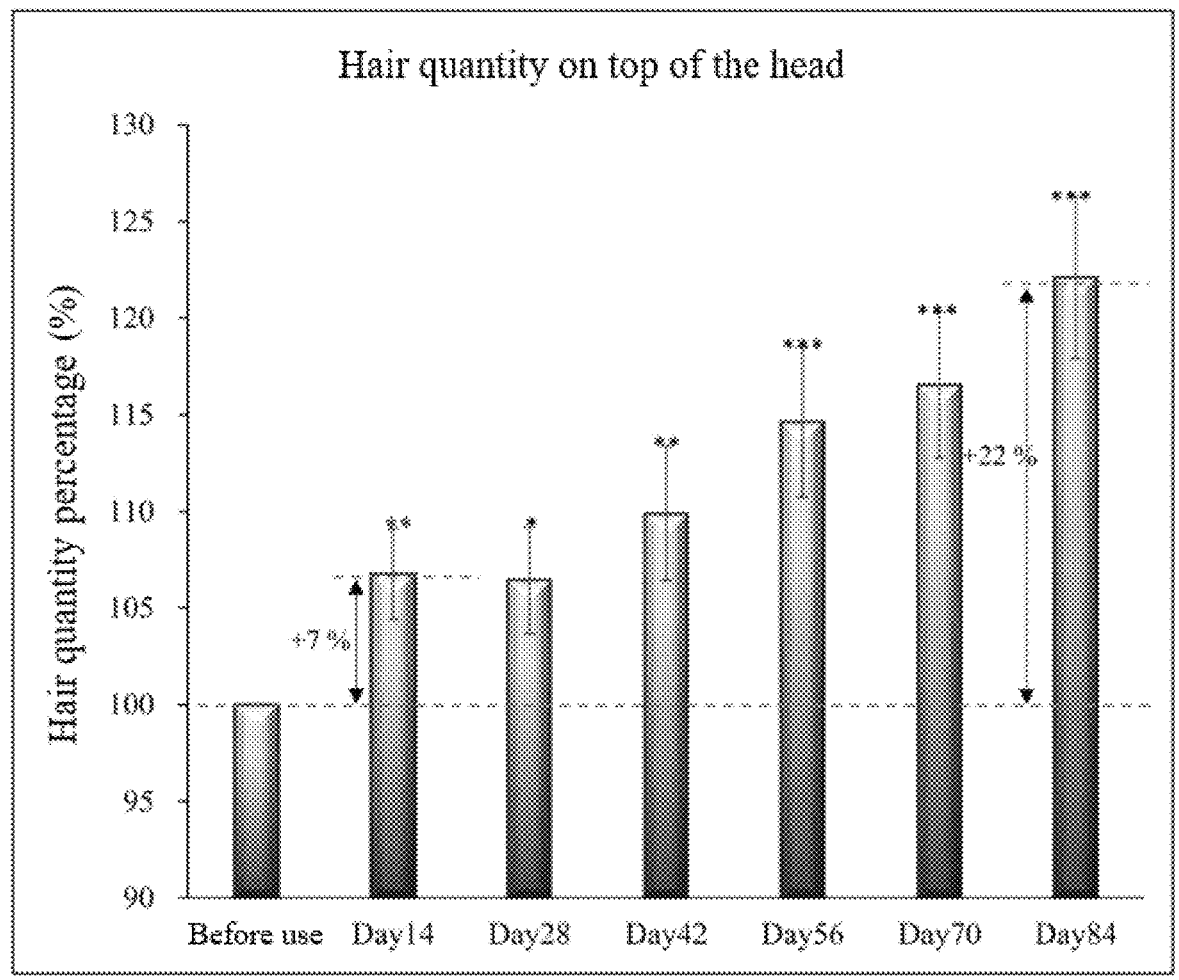
FIG. 6 is a histogram of the hair quantity on top of the head after using the hair care product.

The results of hair quantity on top of participant's head are shown in FIG. 6. The hair quantity percentage on top of the head comparing to that before the treatment (100%) has increased over the past 14 days. Data are presented in Mean Standard deviation (Mean SE, N=20), and starred results indicate significant difference between before using and after using the hair care product (*p<0.05, p<0.01, *p<0.001).

The results of hair quantity on top of participant's head are shown in FIG. 6. From FIG. 6, the hair quantity on top of head gradually increases after using the hair care product of the present invention. It increased by 7% after 14 days of using the hair care product, and increased by 22% after 84 days.
[Hair Quantity Test (Front Hairline)]

This test uses the 60× lens of the scalp hair analysis device to shoot participant's front hairline. The device can automatically select an area for calculation and calculate the hair quantity per square centimeter in the selected area.

Figure 7:
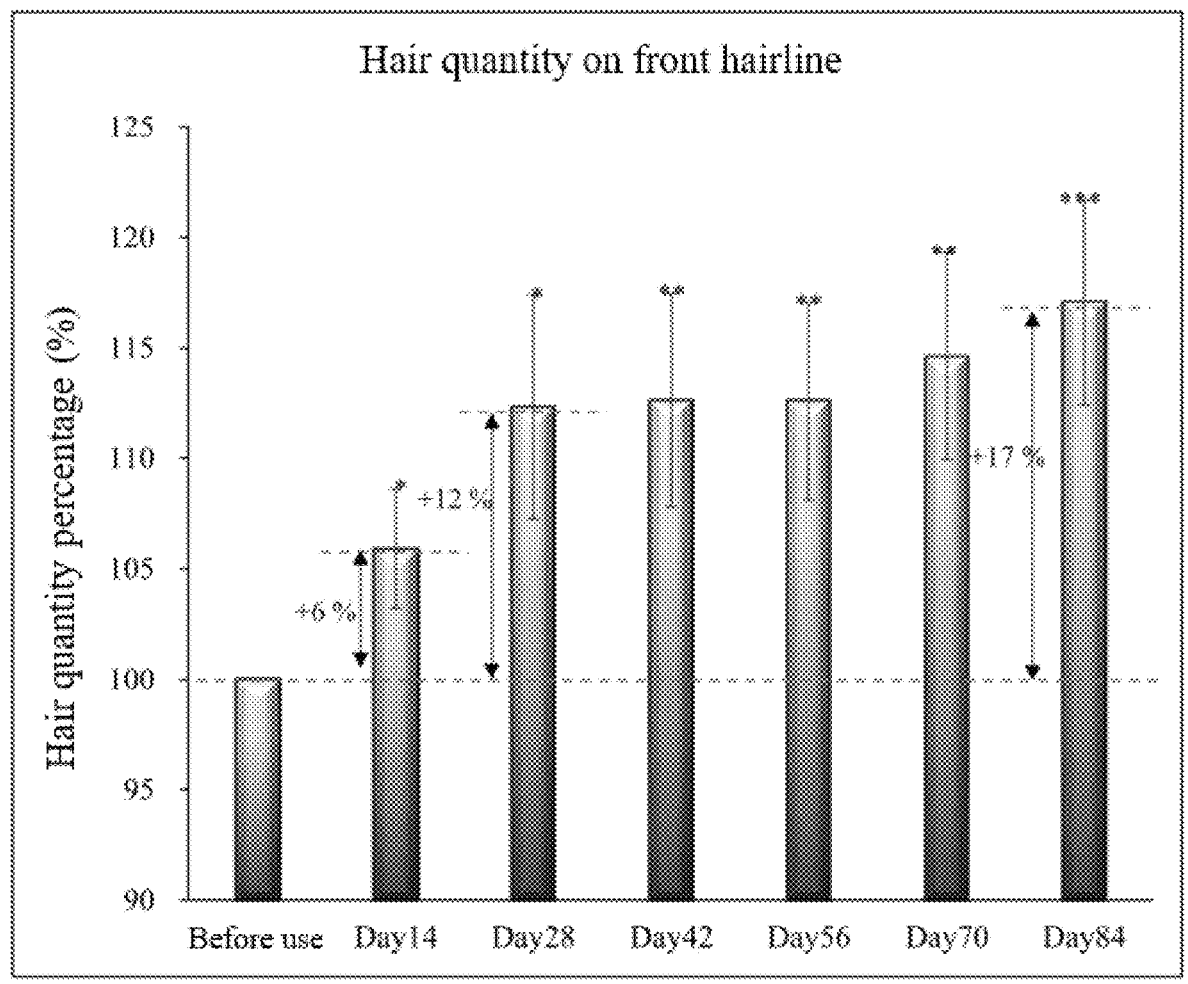
FIG. 7 is a histogram of the hair quantity on front hairline after using the hair care product.

The results of hair quantity on participant's front hairline are shown in FIG. 7. The hair quantity percentage on front hairline comparing to that before the treatment (100%) has increased over the past 14 days. Data are presented in Mean Standard deviation (Mean SE, N=20), and starred results indicate significant difference between before using and after using the hair care product (*p<0.05, p<0.01, *p<0.001).

The results of hair quantity on participant's front hairline are shown in FIG. 7. The hair quantity at front hairline increased 6% after using the hair care product of the present invention for 14 days. It increased 12% after 28 days comparing to before use. Although the quantity gradually increases from day 28 to day 70, the results appear to be reaching a plateau. After 84 days of use, the quantity increased 17% comparing to before use and the results are still significant.
[Hair Thickness Test (Top of the Head)]

This test uses the 200× lens of the scalp hair analysis device to shoot the hair on top of participant's head. The hair thickness (in millimeter) was calculated by software in the device and converted into the cross sectional area of the hair.

Figure 8:
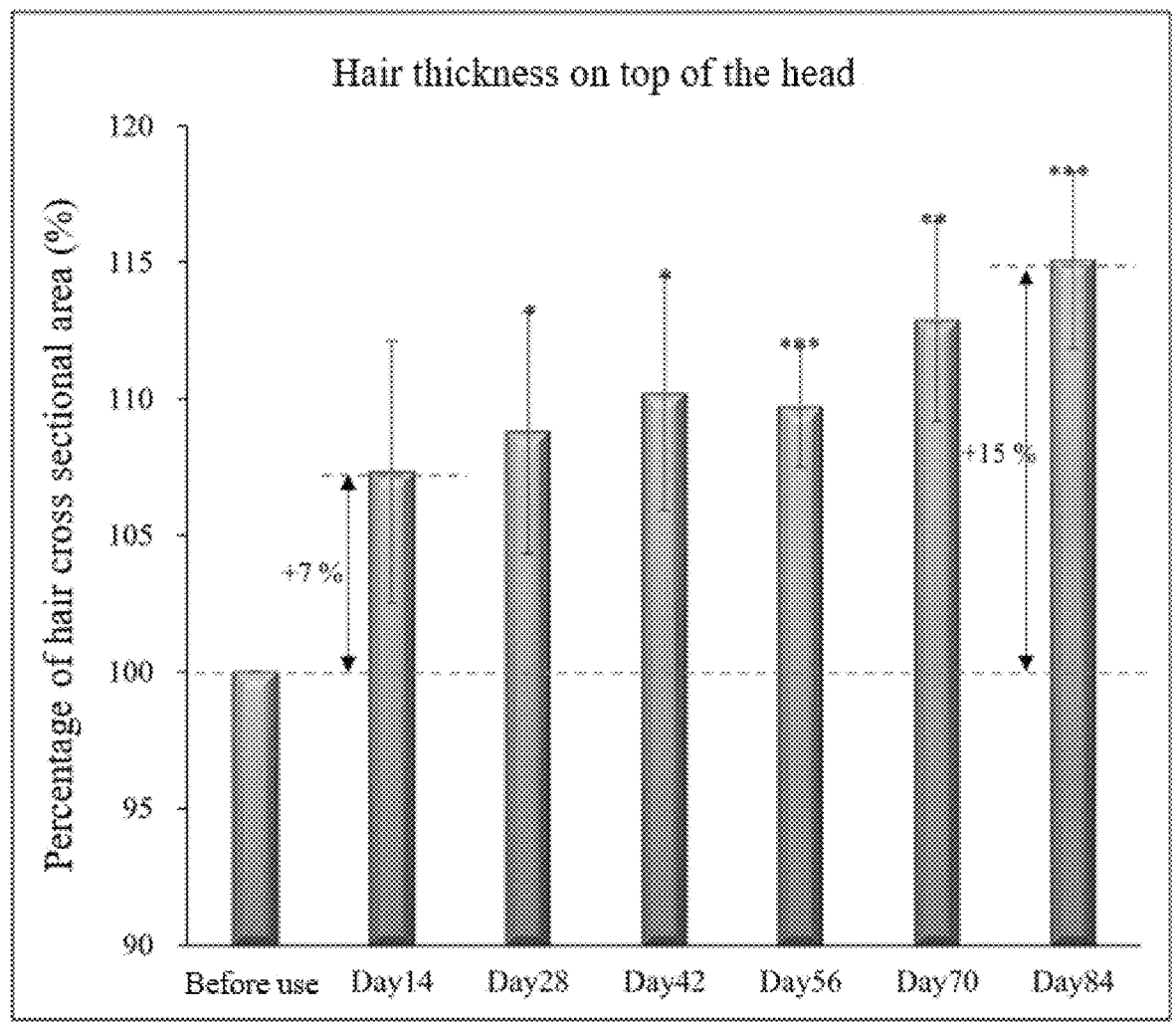
FIG. 8 is a histogram of the thickness of hair on top of the head after using the hair care product.

The results of hair thickness on top of participant's head are shown in FIG. 8. The hair cross sectional area percentage on top of the head comparing to that before the treatment (100%) has increased over the past 14 days. Data are presented in Mean Standard deviation (Mean SE, N=20), and starred results indicate significant difference between before using and after using the hair care product (*p<0.05, p<0.01, *p<0.001).

The results of hair thickness on top of participant's head are shown in FIG. 8. From FIG. 8, the hair cross sectional area on top of the participant's head is gradually increasing. It increased 7% after 14 days of using the product, and increased 15% after 84 days of use comparing to the condition before use.
[Hair Thickness Test (Front Hairline)]

This test uses the 200× lens of the scalp hair analysis device to shoot the participant's front hairline. The hair thickness (in millimeter) was calculated by software in the device and converted into the cross sectional area of the hair.

Figure 9:
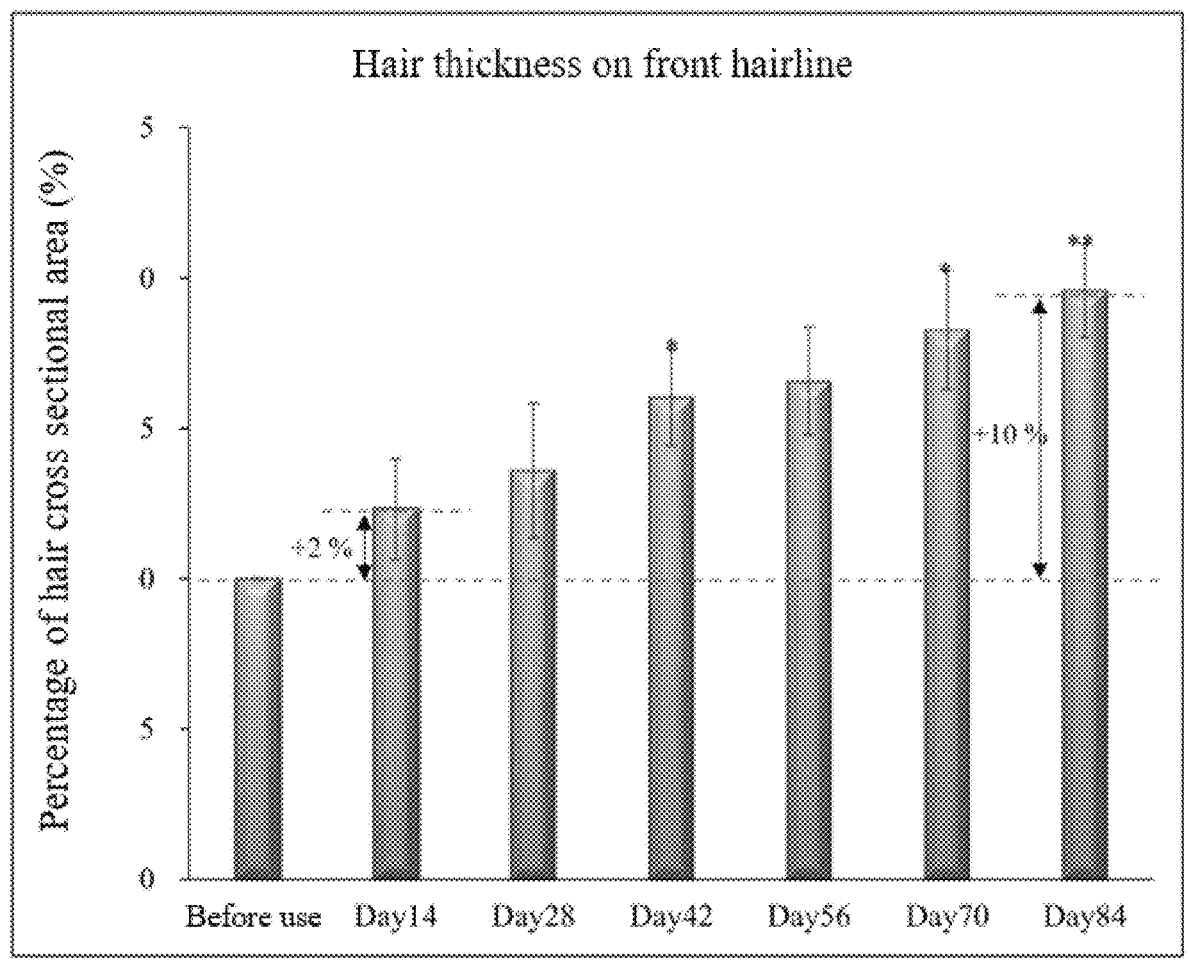
FIG. 9 is a histogram of the thickness of hair on front hairline after using the hair care product.

The results of hair thickness on participant's front hairline are shown in FIG. 9. The hair cross-sectional area percentage on the front hairline comparing to that before the treatment (100%) has increased over the past 14 days. Data are presented in Mean Standard deviation (Mean SE, N=20), and starred results indicate significant difference between before using and after using the hair care product (*p<0.05, **p<0.01).

The results of hair thickness on participant's front hairline are shown in FIG. 9. From FIG. 9, the hair cross-sectional area on top of the participant's head is gradually increasing. It increased 2% after 14 days of using the product, and increased 10% after 84 days of use comparing to the condition before use.
[Sebum Level Test]

This test uses a Sebumeter SM815 probe to measure the sebum level of scalp. The higher value indicates more transmittance and higher sebum level of the participant.

Figure 10:
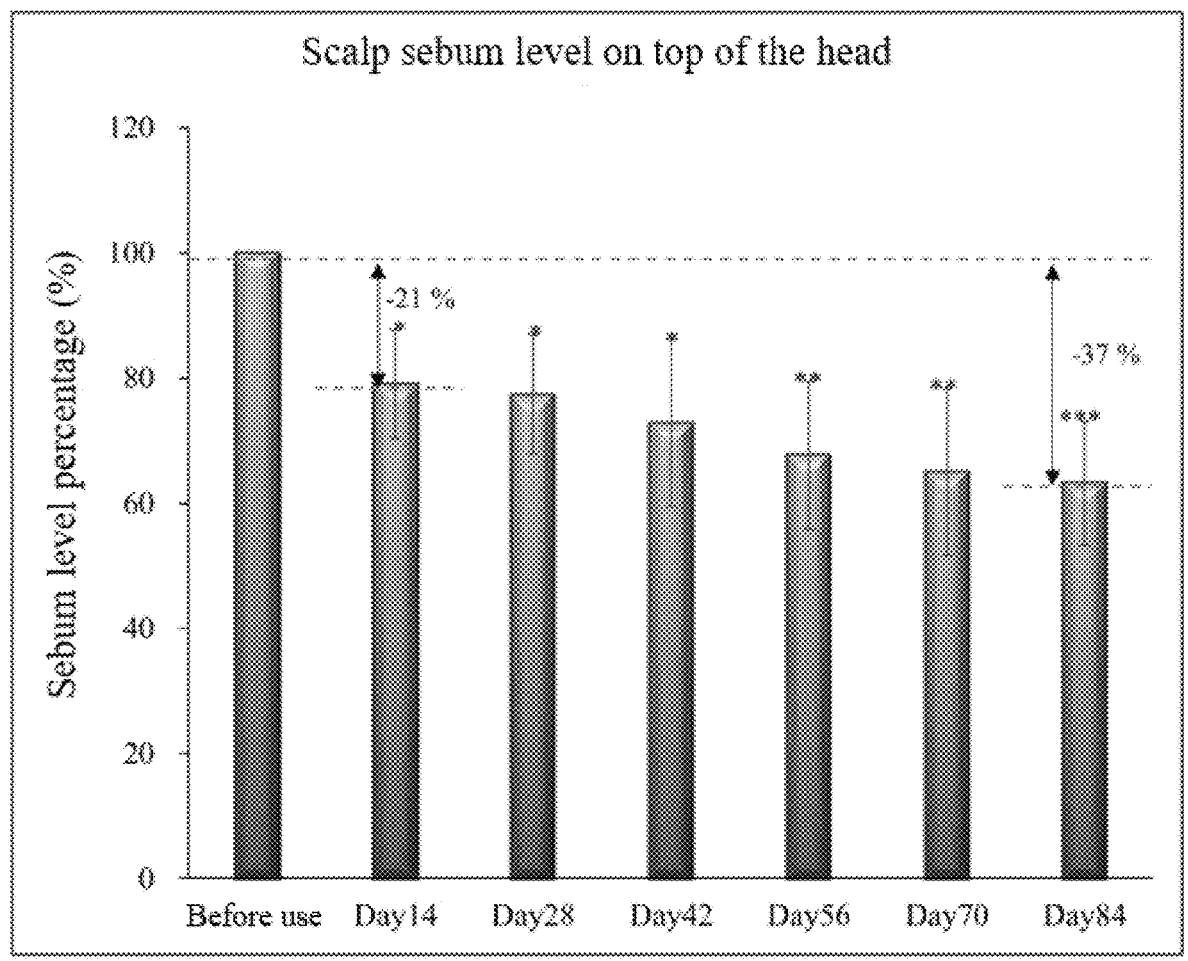
FIG. 10 is a histogram of sebum level on scalp after using the hair care product.

Referring to FIG. 10, the results of participant's sebum level on scalp, the sebum level percentage gradually decreases after 14 days of using the hair care product comparing to that before use (100%). Data are presented in Mean Standard deviation (Mean SE, N=20), and starred results indicate significant difference between before use and after use (*p<0.05, **p<0.01).

The results of the participant's scalp sebum level are shown in FIG. 10. After using the hair care product of this invention, the sebum level on top of head gradually decreases. After 14 days of using the hair care product, the sebum level decreases 21%, and after 84 days it significantly decreases 37% comparing to the level before using the hair care product.

[Percentage of Improvement Among Participants]

After analyzing the results of 20 participants using the hair care product of present invention, more than 70% of participants have shown improvement in their hair condition. More specifically, over 80% of participants have shown improvement regarding hair quantity on top of the head, hair thickness on top of the head and scalp sebum level. Detail data are shown in Table 1.

TABLE 1

| After using the hair care product for 84 days | Improvement percentage (%)* |
|---|---|
| Hair quantity on top of the head | 85% |
| Hair quantity on front hairline | 75% |
| Hair thickness on top of the head | 85% |
| Hair thickness on front hairline | 70% |
| Scalp sebum level | 80% |

*Improvement percentage (%) = number of people improved/total number of participants × 100

[Satisfaction Rate Among Participants After Using the Hair Care Product]

Figure 11:
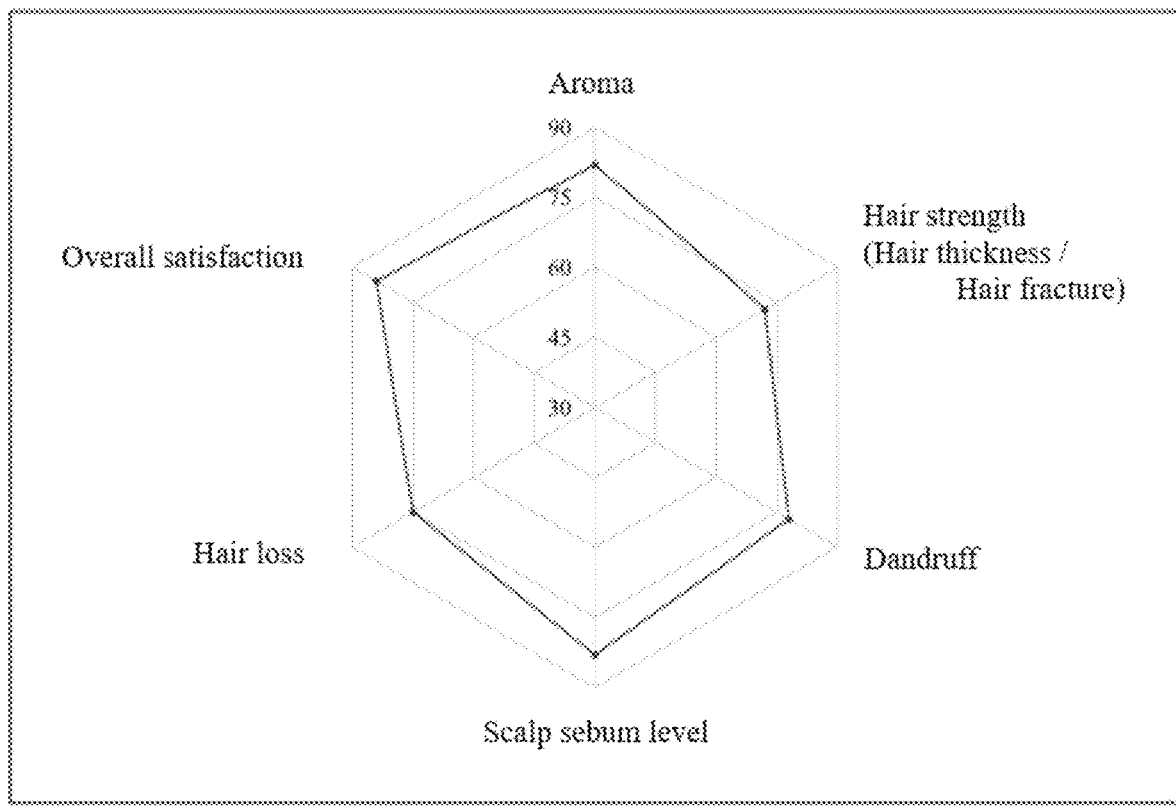
FIG. 11 is the satisfaction result of users after using the hair care product.
Figure 12:
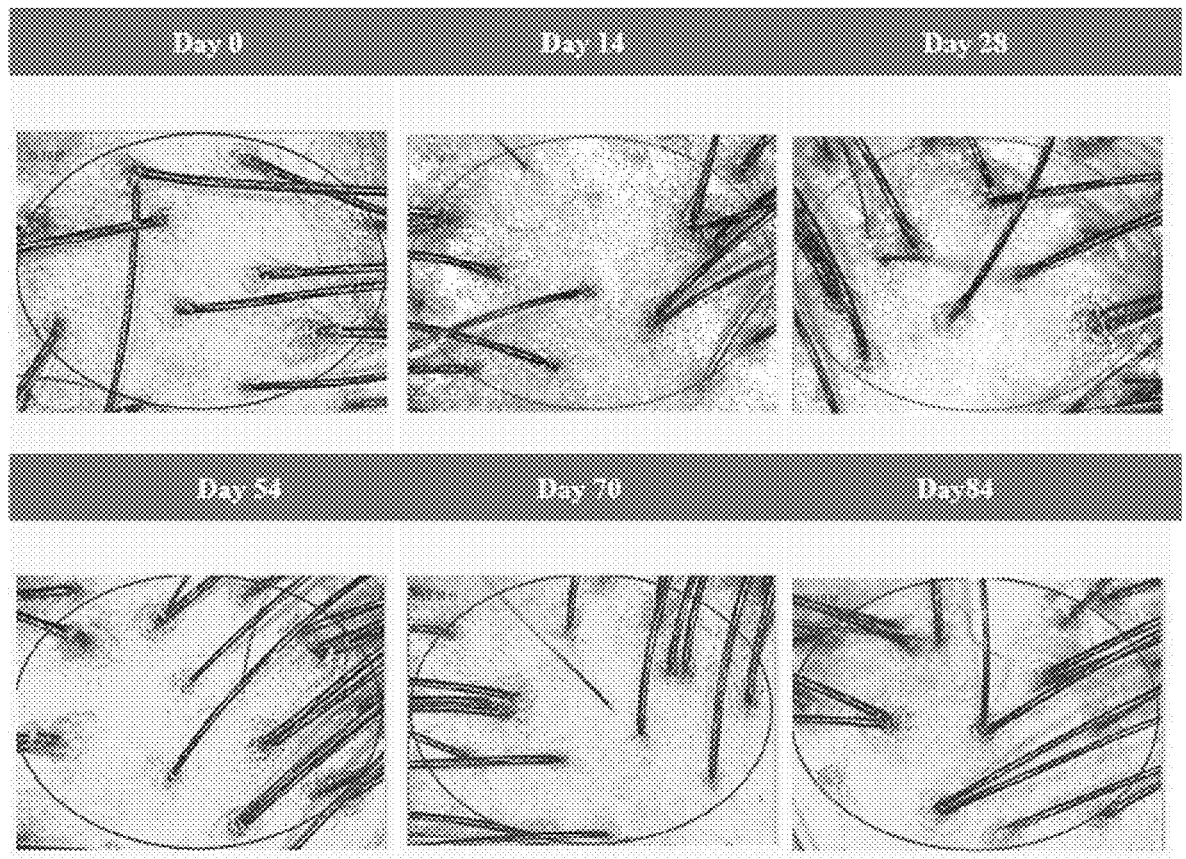
FIG. 12 is a comparison picture of the hair quantity on top of a participant's head after using the hair care product on day 0, day 14, day 28, day 56, day 70 and day 84 using the scalp hair analysis device.
Figure 13:
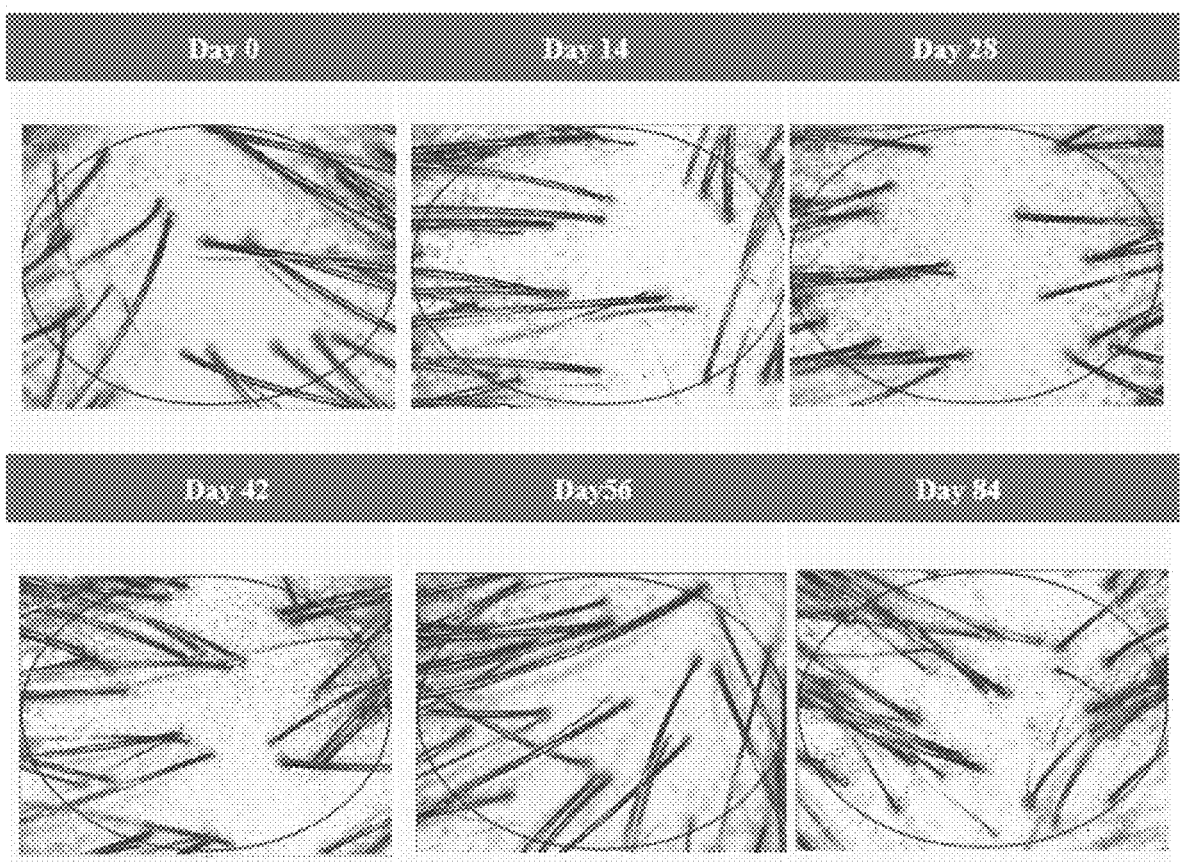
FIG. 13 is a comparison picture of the hair quantity on a participant's hairline after using the hair care product on day 0, day 14, day 28, day 56, day 70 and day 84 taken by the scalp hair analysis device.
Figure 14:
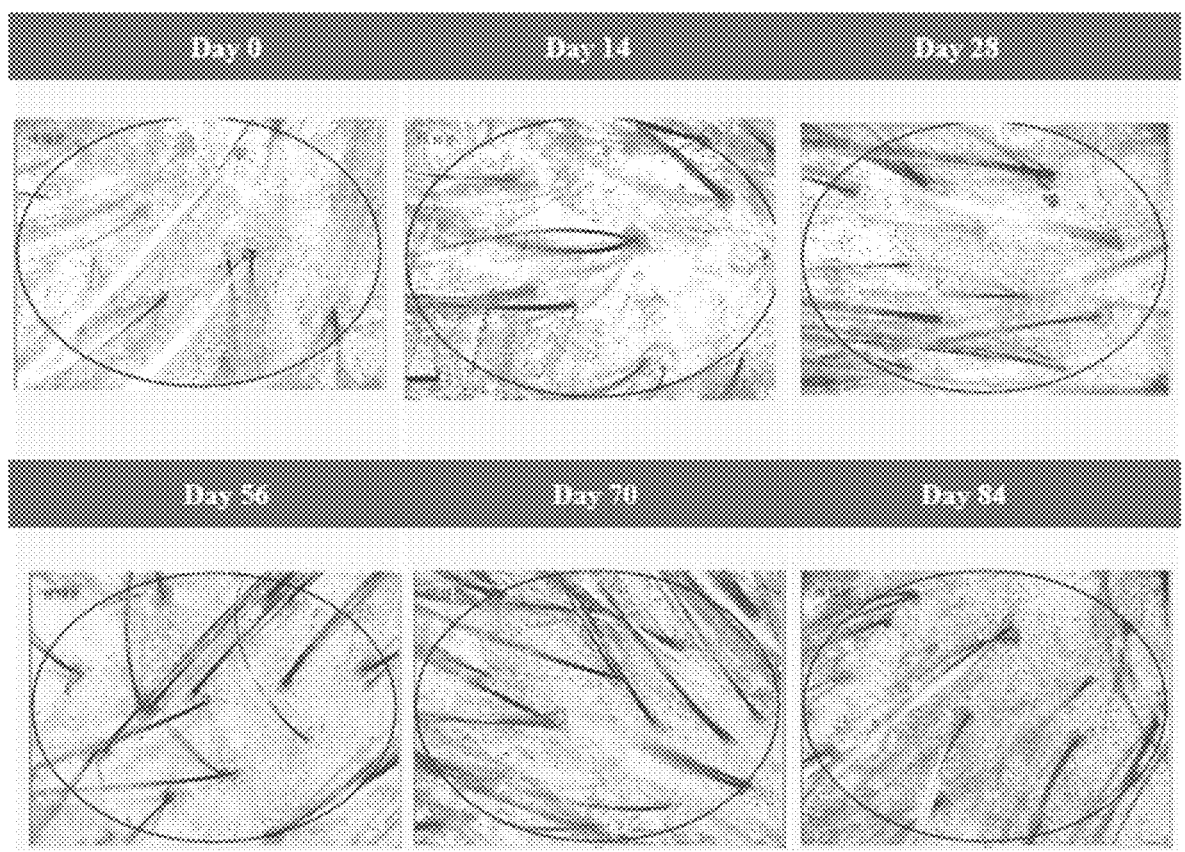
FIG. 14 is a comparison picture of the hair quantity on another participant's hairline after using the hair care product on day 0, day 14, day 28, day 56, day 70 and day 84 taken by the scalp hair analysis device.
Figure 15:
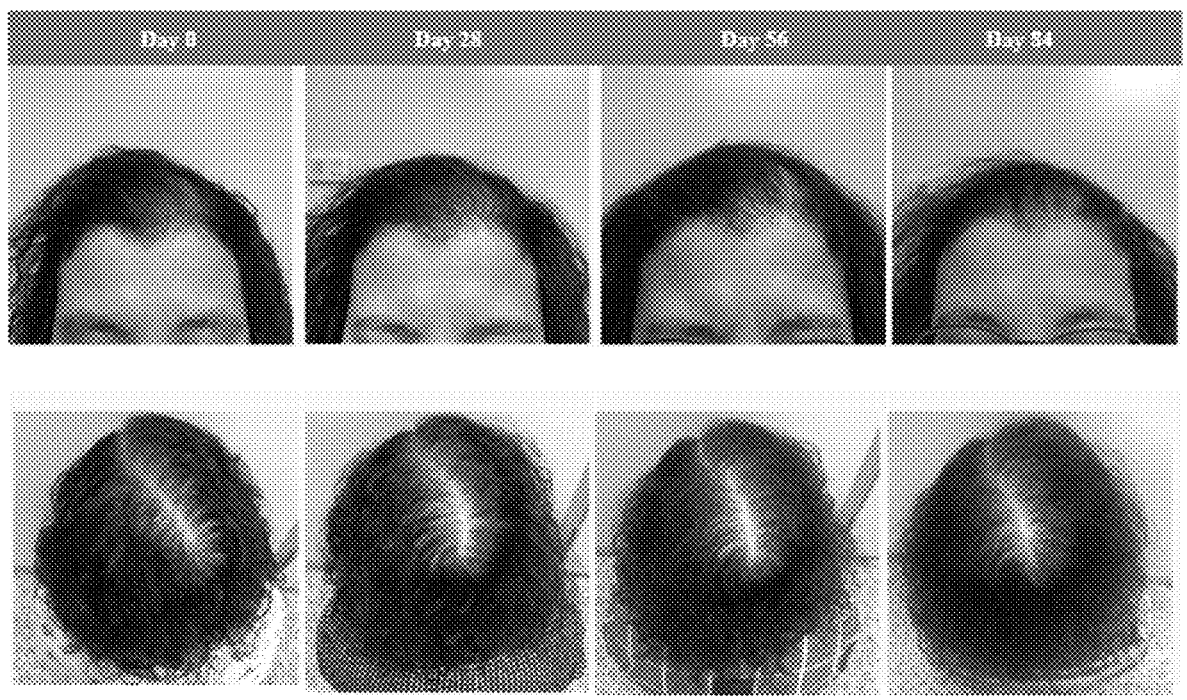
FIGS. 15, 16, 17, 18, 19 and 20 are pictures of the hair quantity on hairline and top of 6 participants' head after using the hair care product on day 0, day 14, day 28, day 56, day 70 and day 84.
Figure 16:
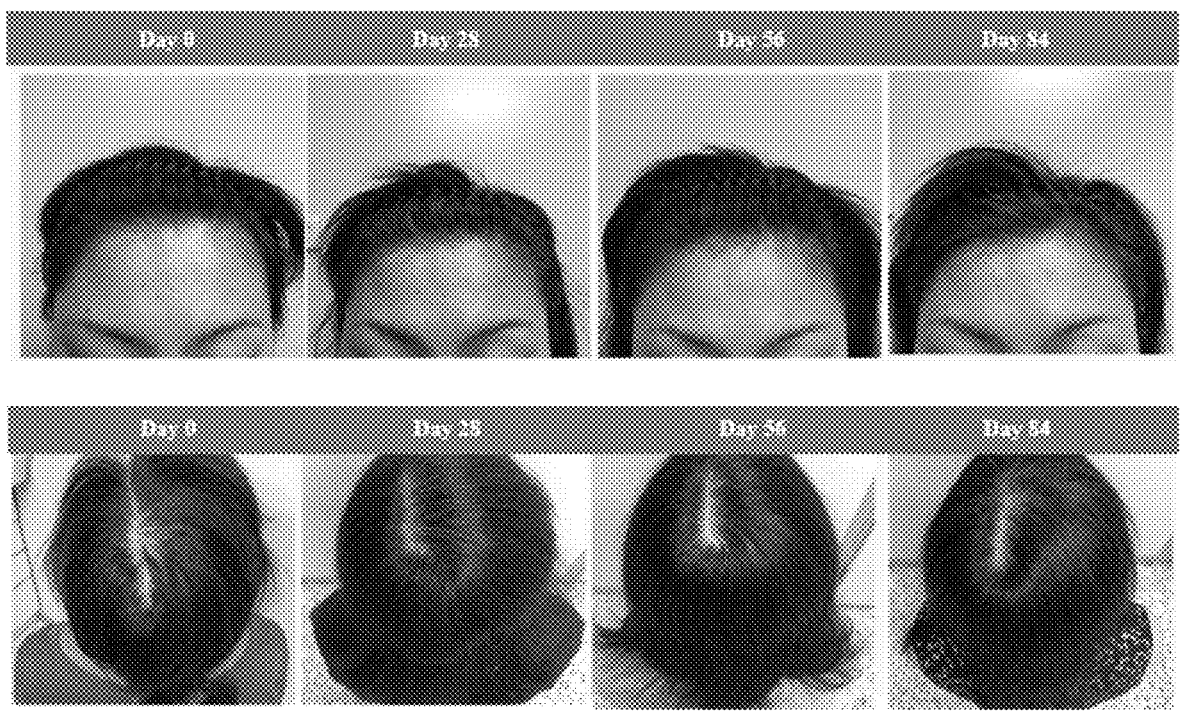
Figure 17:
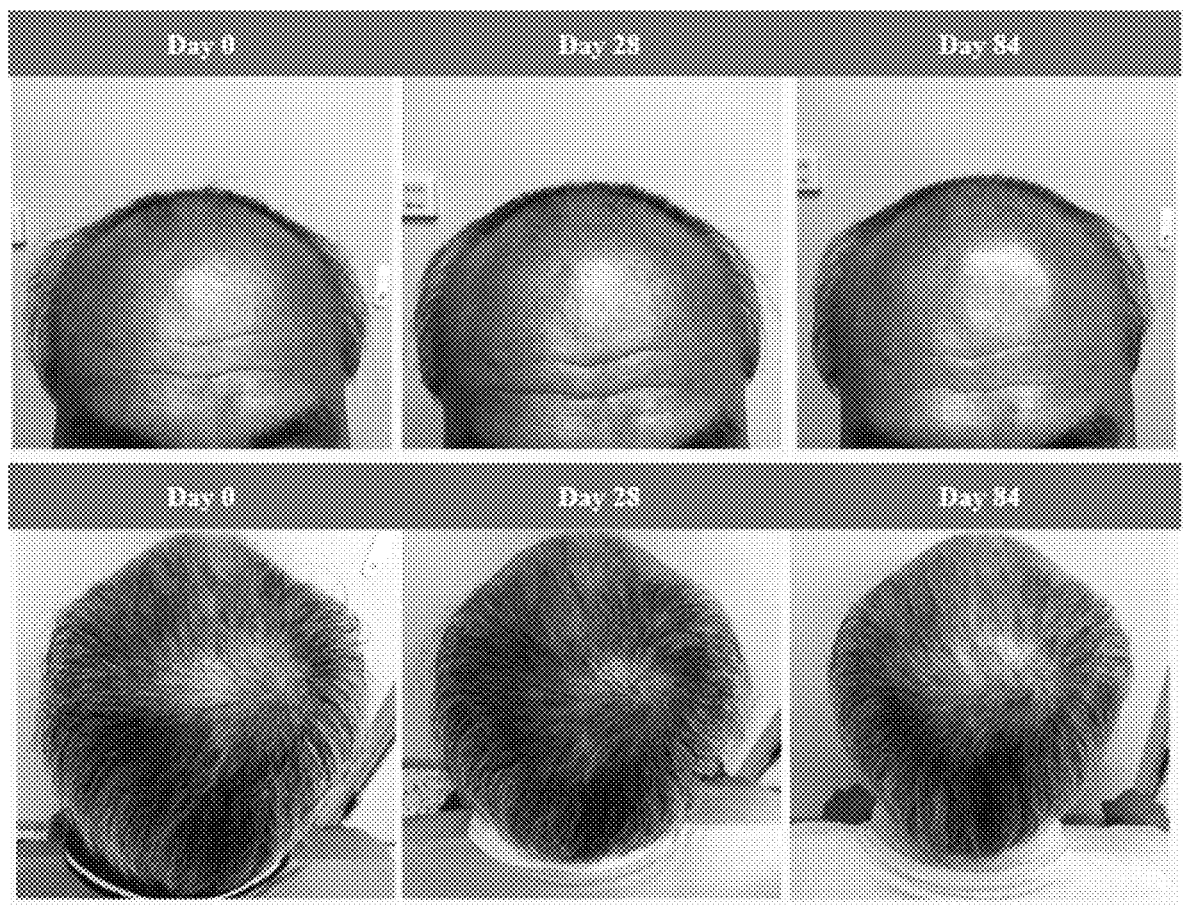
Figure 18:
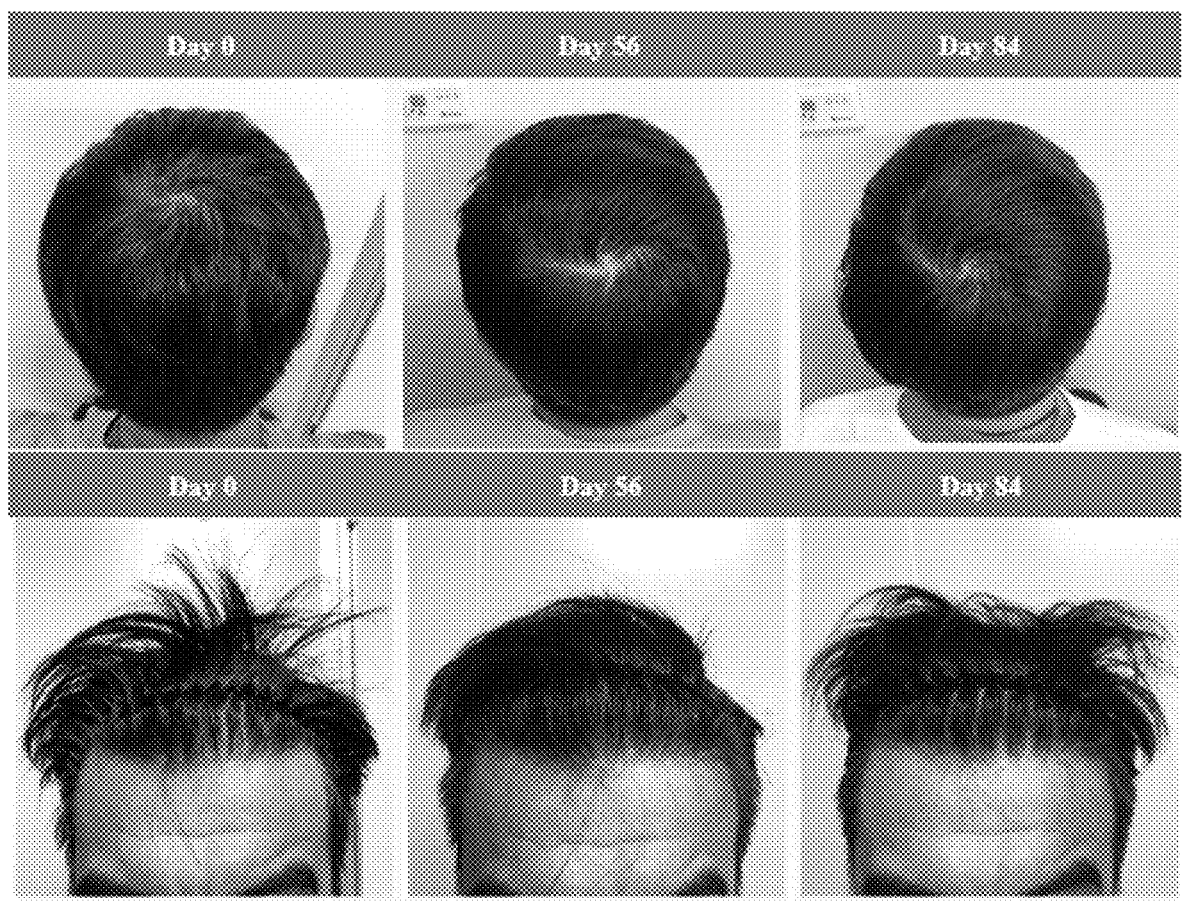
Figure 19:
Figure 20:
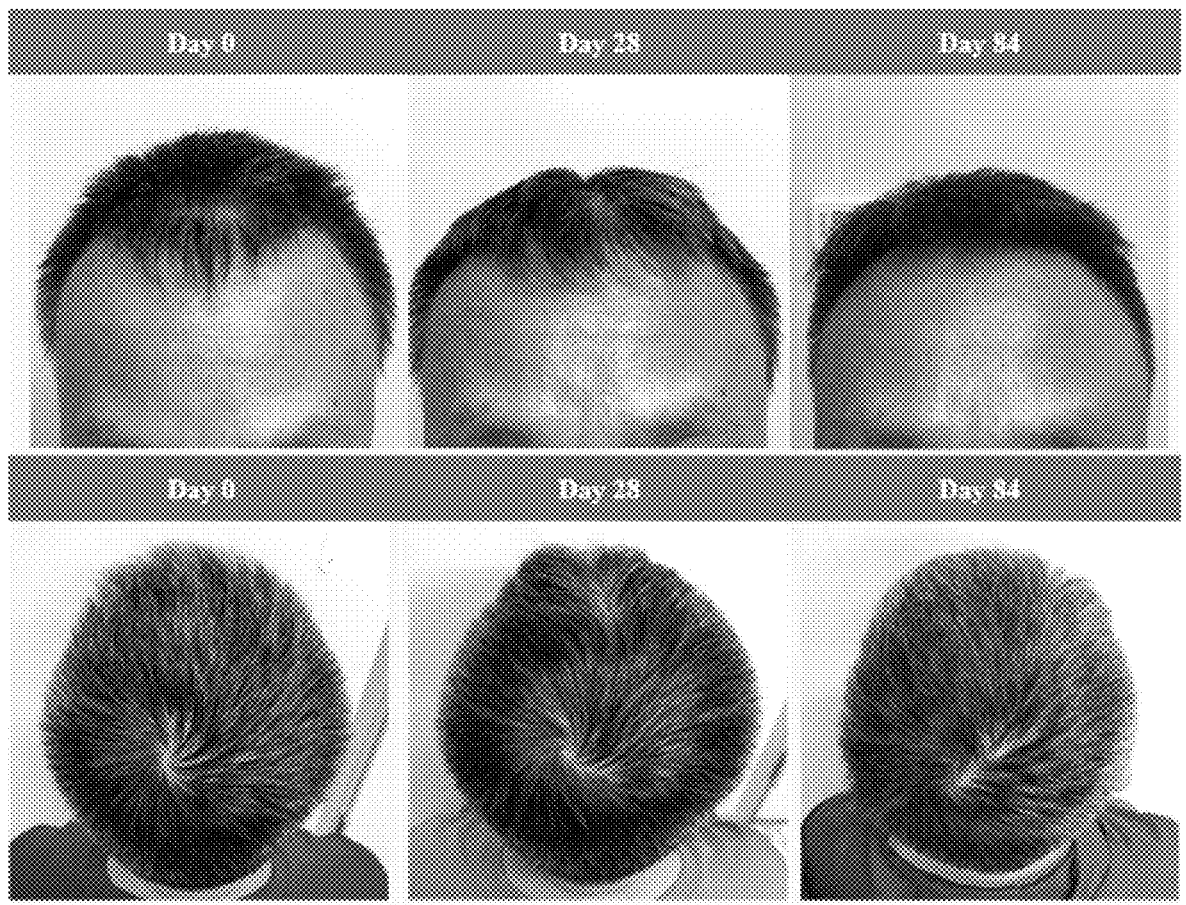
Figure 21:
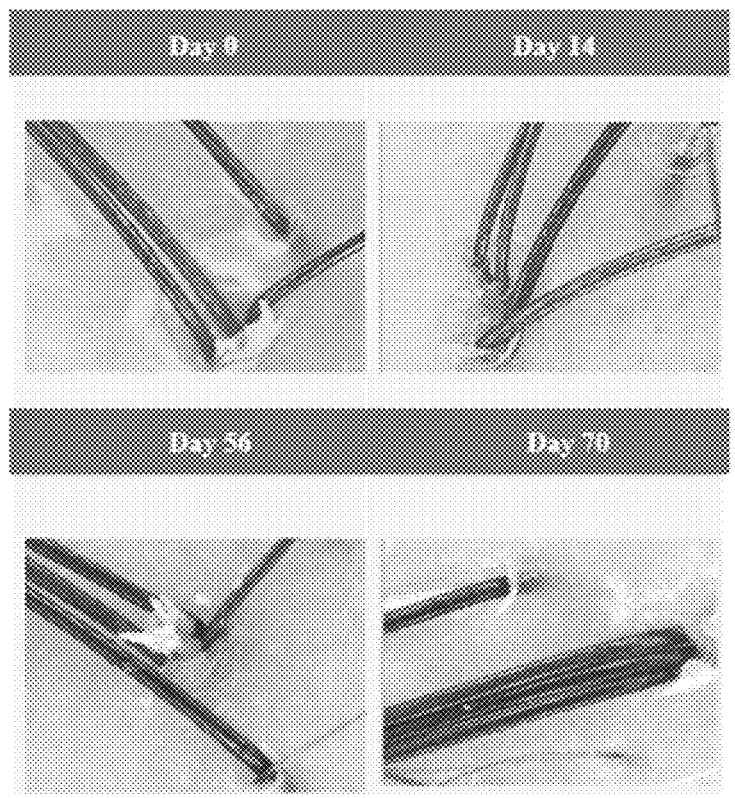
FIG. 21 is a comparison picture of the hair thickness on top of a participant's head after using the hair care product on day 0, day 14, day 56 and day 70 taken by the scalp hair analysis device.
Figure 22:
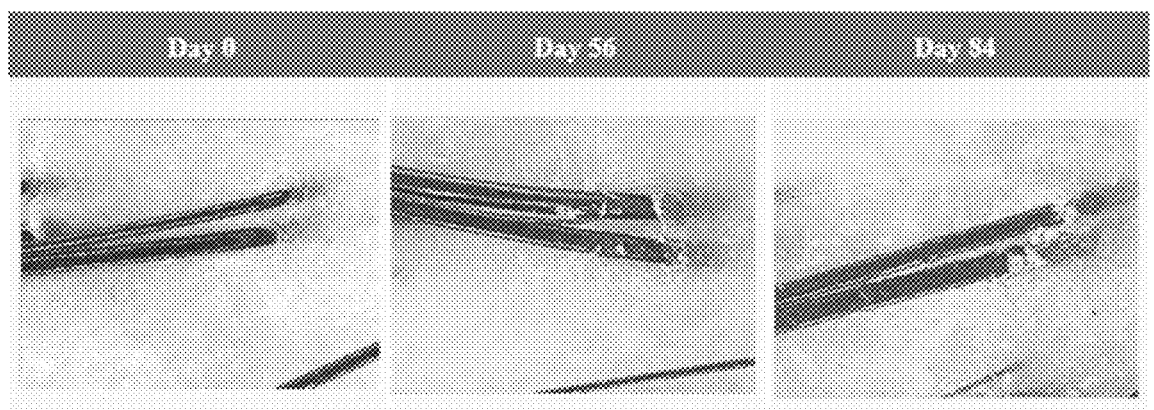
FIG. 22 is a comparison picture of the hair thickness at a participant's hairline after using the hair care product on day 0, day 56 and day 84 taken by the scalp hair analysis device.
Figure 23:
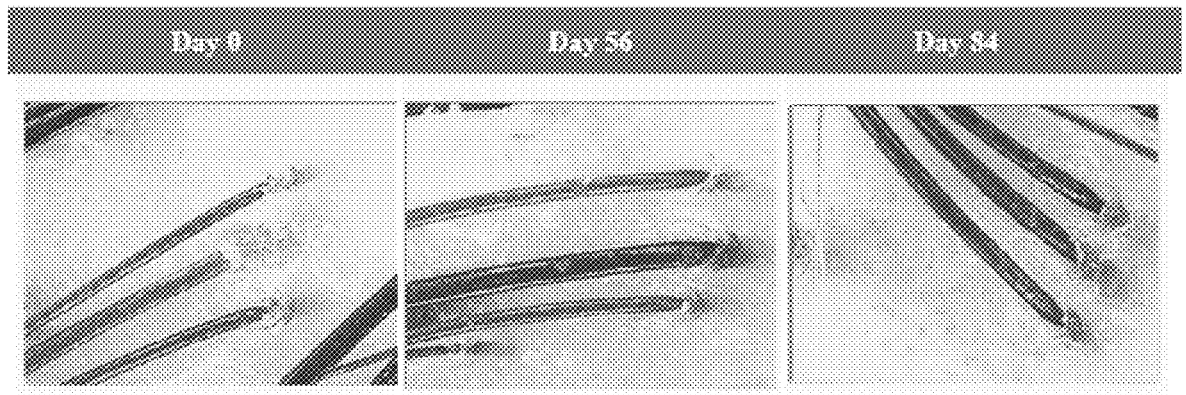
FIG. 23 is a comparison picture of the hair thickness at another participant's hairline after using the hair care product on day 0, day 56 and day 84 taken by the scalp hair analysis device.
Figure 24:
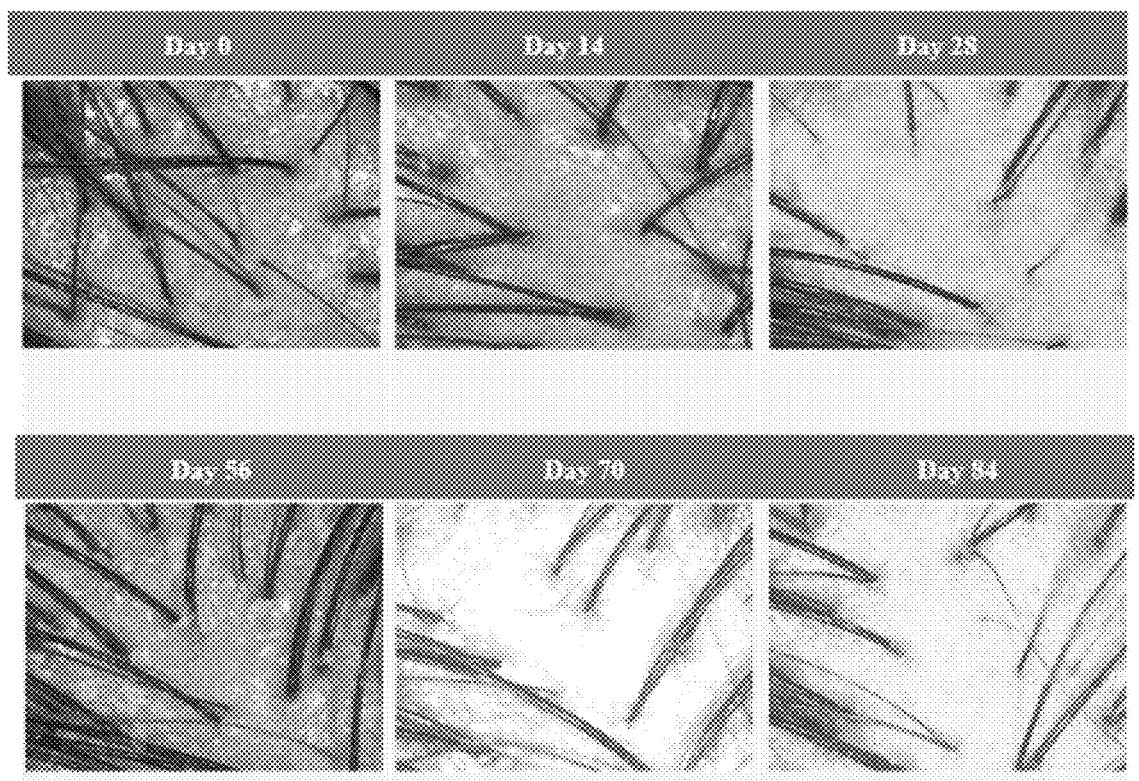
FIG. 24 is a comparison picture of a participant's scalp sebum level after using the hair care product on day 0, day 14, day 28, day 56, day 70 and day 84 taken by the scalp hair analysis device.
Figure 25:
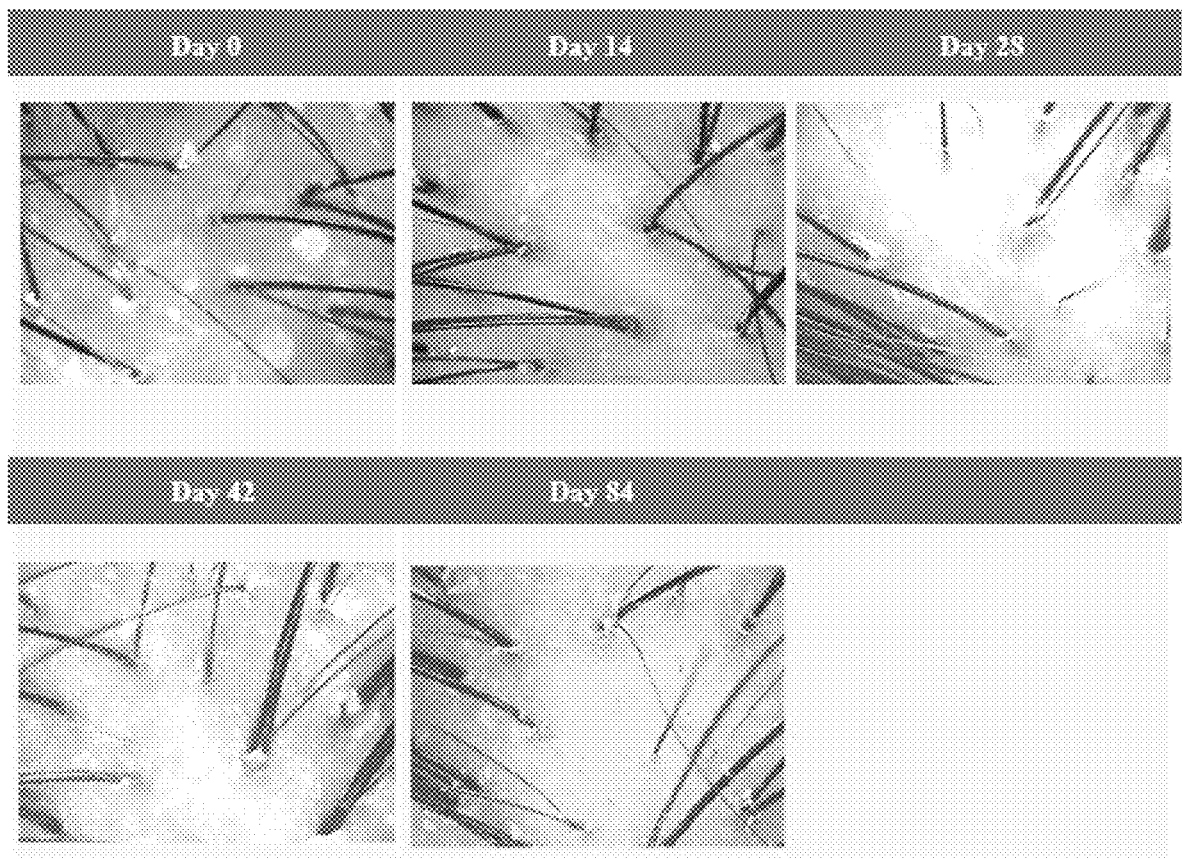
FIG. 25 is a comparison picture of a participant's dandruff condition after using the hair care product on day 0, day 14, day 28 and day 84 taken by the scalp hair analysis device.
Figure 26:
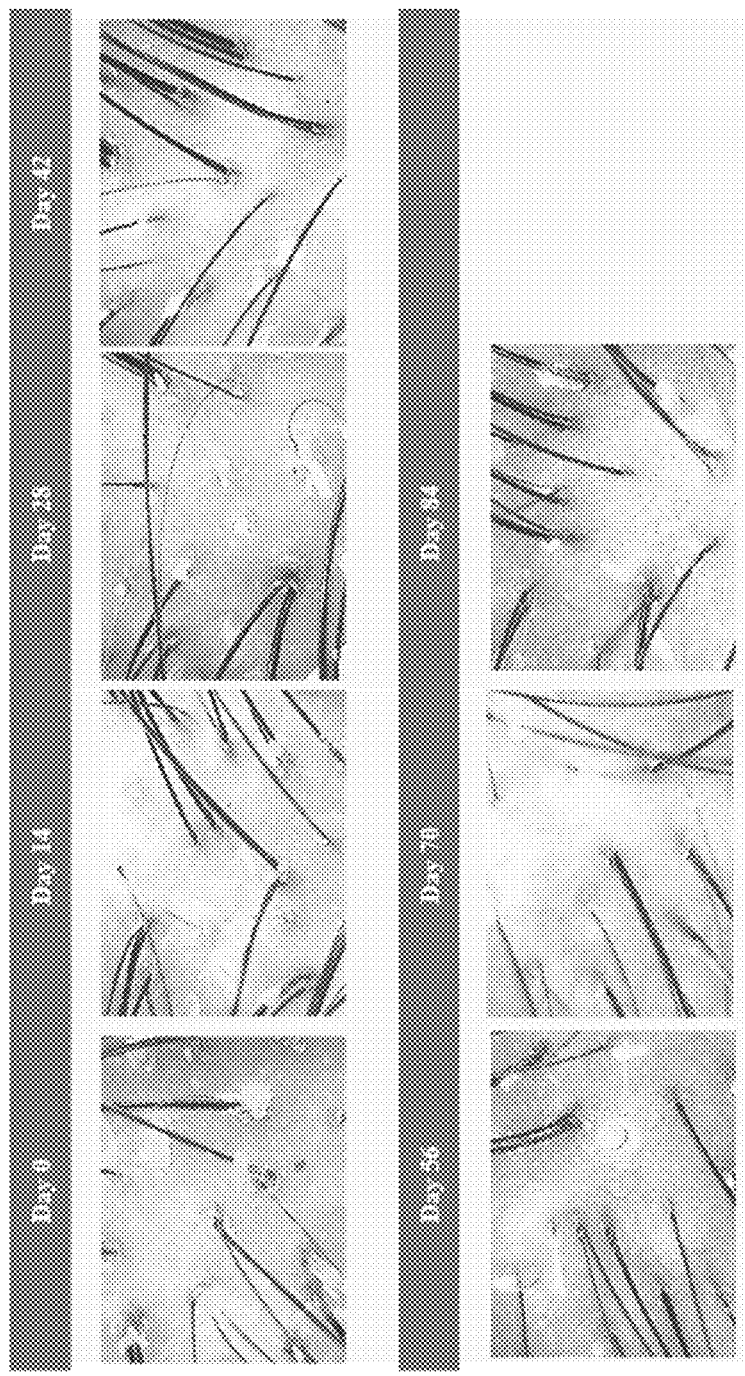
FIG. 26 is a comparison picture of a participant's dandruff condition after using the hair care product on day 0, day 14, day 28, day 70 and day 84 taken by the scalp hair analysis device

FIG. 11 is the satisfaction rate among 20 participants after using the hair product in present invention for 84 days. 20 participants were asked to rate their hair strength (hair thickness, hair fracture), hair loss, dandruff, scalp sebum level from 1 to 5. Results showed that the overall satisfaction rate among participants was 84%, especially the improvement of scalp sebum level (83%), dandruff (78%), hair loss(75%) are most significant among participants.

The results of aforementioned tests are shown as mean relative percentage in Table 2.

TABLE 2

| | Before use | 14 days | 28 days | 42 days | 56 days | 70 days | 84 days |
|---|---|---|---|---|---|---|---|
| Hair quantity on top of the head (%) | 100 | 107 | 106 | 110 | 115 | 117 | 122 |
| Hair quantity on front hairline (%) | 100 | 106 | 112 | 113 | 113 | 115 | 117 |
| Hair thickness on top of the head (cross sectional area %) | 100 | 107 | 109 | 110 | 110 | 113 | 115 |
| Hair thickness at front hairline (cross sectional area %) | 100 | 102 | 104 | 106 | 107 | 108 | 110 |
| Scalp sebum level (%) | 100 | 79 | 77 | 73 | 68 | 65 | 63 |

Moreover, in FIGS. 12 through 26, 6 individuals are randomly selected out of 20 participants to observe and record the condition of hair on day 0, day 14, day 28, day 42, day 56, day 70 and day 84.

From the above tests, it can be concluded that the hair care product can improve scalp sebum condition and increase hair growth.

The nano composite material can be used in topical preparations for skin, hair loss prevention compound, hair growth promotion products to facilitate skin repair, hair loss prevention and hair growth promotion.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

What is claimed is:

1. A nano composite material, comprising: a biotinoyl tripeptide-1 nanosilver composite material which is conjugated by biotinoyl tripeptide-1 and nanosilver, wherein the Zeta potential of the biotinoyl tripeptide-1 nanosilver is greater than ±15 mv.

2. The nano composite material of claim 1, wherein the biotinoyl tripeptide-1 nanosilver composite is analyzed in the form of nanosilver aqueous solution by an ultraviolet/visible spectrophotometer; the absorption spectrum has a specific absorption spectrum peak within 385 nm to 415 nm.

3. The nano composite material of claim 1, wherein the particle size of the biotinoyl tripeptide-1 nanosilver composite is between 20 nm to 100 nm.

4. The nano composite material of claim 2, wherein the particle size of the biotinoyl tripeptide-1 nanosilver composite is between 20 nm to 100 nm.

5. A topical preparation for skin, comprising the nano composite material of claim 1.

6. A compound to prevent hair loss, comprising the nano composite material of claim 1.

7. A solution for promoting hair growth, comprising the nano composite material of claim 1.

8. A solution for promoting eyelash growth, comprising the nano composite material of claim 1.

* * * * *